(12) United States Patent
Willis

(10) Patent No.: US 8,388,540 B2
(45) Date of Patent: Mar. 5, 2013

(54) METHOD AND APPARATUS FOR ORIENTING A MEDICAL IMAGE

(75) Inventor: N. Parker Willis, Atherton, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 3804 days.

(21) Appl. No.: 10/319,285

(22) Filed: Dec. 13, 2002

(65) Prior Publication Data

US 2004/0114146 A1    Jun. 17, 2004

(51) Int. Cl.
*A61B 8/14* (2006.01)
(52) U.S. Cl. .................. 600/462; 600/459
(58) Field of Classification Search .......... 600/4, 59, 600/407, 424, 437–469
See application file for complete search history.

(56) References Cited

U.S. PATENT DOCUMENTS

| | | |
|---|---|---|
| 4,176,662 A | 12/1979 | Frazer |
| 4,757,821 A | 7/1988 | Snyder |
| 4,841,977 A | 6/1989 | Griffith et al. |
| 5,391,199 A | 2/1995 | Ben-Haim |
| 5,406,951 A | 4/1995 | ten Hoff et al. |
| 5,538,004 A | 7/1996 | Bamber |
| 5,655,537 A | 8/1997 | Crowley |
| 5,704,361 A | 1/1998 | Seward et al. |
| 5,724,978 A | 3/1998 | Tenhoff |
| 5,848,969 A | 12/1998 | Panescu et al. |
| 5,876,345 A * | 3/1999 | Eaton et al. ............ 600/466 |
| 5,938,602 A | 8/1999 | Lloyd |
| 5,954,649 A | 9/1999 | Chia et al. |
| 5,983,126 A | 11/1999 | Wittkampf |
| 6,045,508 A * | 4/2000 | Hossack et al. ............ 600/447 |
| 6,063,022 A | 5/2000 | Ben-Haim |
| 6,083,170 A | 7/2000 | Ben-Haim |
| 6,102,865 A | 8/2000 | Hossack et al. |
| 6,171,248 B1 * | 1/2001 | Hossack et al. ............ 600/459 |
| 6,216,027 B1 | 4/2001 | Willis et al. |
| 6,224,556 B1 | 5/2001 | Schwartz et al. |
| 6,332,089 B1 | 12/2001 | Acker et al. |
| 6,347,240 B1 | 2/2002 | Foley et al. |
| 6,361,500 B1 | 3/2002 | Masters |
| 6,364,840 B1 | 4/2002 | Crowley |
| 6,429,861 B1 | 8/2002 | Hossack et al. |
| 6,434,415 B1 | 8/2002 | Foley et al. |
| 6,450,964 B1 | 9/2002 | Webler |
| 6,456,864 B1 | 9/2002 | Swanson et al. |
| 6,471,648 B1 | 10/2002 | Gamelsky et al. |
| 6,490,467 B1 | 12/2002 | Bucholz et al. |
| 6,490,474 B1 | 12/2002 | Willis et al. |

\* cited by examiner

*Primary Examiner* — Sanjay Cattungal
(74) *Attorney, Agent, or Firm* — Seager, Tufte & Wickhem, LLC

(57) ABSTRACT

The present invention provides systems, methods, and devices for orienting image data derived from body tissue. An imaging assembly is introduced into the body of a patient and rotated about an axis. A tracking beam mechanically associated with the imaging assembly is generated, such that the tracking rotates about the axis in unison with the imaging assembly. An angle that the rotating tracking beam makes between a reference rotational orientation and a reference point is determined. The reference rotational orientation can be associated with a fiducial point within the ultrasound image data, such that the ultrasound image can be oriented based on the determined tracking beam rotation angle.

39 Claims, 6 Drawing Sheets

METHOD AND APPARATUS FOR ORIENTING A MEDICAL IMAGE

FIELD OF THE INVENTION

The present inventions generally relate to medical imaging devices and methods, and more particularly to systems and methods for ultrasonically imaging body tissue.

BACKGROUND OF THE INVENTION

For purposes of diagnosis and treatment planning, imaging techniques are commonly used in medical procedures to view the internal anatomy of a patient's body. In one imaging technique, an imaging catheter with a rotatable ultrasound transducer mounted on its tip is inserted into the patient's body, e.g., through a blood vessel. To obtain an interior image of the body, the rotating ultrasound transducer emits pulses of ultrasound energy into the body. A portion of the ultrasound energy is reflected off of the internal anatomy of the body back to the transducer. The reflected ultrasound energy (echo) impinging on the transducer produces an electrical signal, which is used to form a 360 degree cross-sectional interior image of the body. The rotating ultrasound transducer can be longitudinally translated, so that multiple cross-sectional images can be generated and later reconstructed into a three-dimensional interior image of the body.

Oftentimes, it is desirable to properly orient an image generated by the imaging catheter relative to an anatomical structure (such as, e.g., a heart) or a reference point (such as, e.g., the anterior of a patient). Recently, it has become desirable to properly orient an ultrasonically generated local image of body tissue within a global image of a body or organ containing such body tissue. In order to assist physicians in maneuvering medical devices to sites of interest in the body, such global images are typically generated using a guidance system.

In one guidance system, a fluoroscopic image of the device (or at least radiopaque bands located on the device) and surrounding anatomical landmarks (with or without the use of contrast media) in the body are taken and displayed to the physician. The fluoroscopic image enables the physician to ascertain the position of the device within the body and maneuver the device to the site of interest. In another guidance system using anatomic mapping, a graphical representation of the device or portion of the device is displayed in a three-dimensional computer-generated representation of a body tissue, e.g., a heart chamber. The three-dimensional representation of the body tissue is produced by mapping the geometry of the inner surface of the body tissue in a three-dimensional coordinate system, e.g., by moving a mapping device to multiple points on the body tissue. The position of the device to be guided within the body tissue is determined by placing one or more location sensors on the device and tracking the position of these sensors within the three-dimensional coordinate system. An example of this type of guidance system is the Realtime Position Management™ (RPM) tracking system developed commercially by Cardiac Pathways Corporation, now part of Boston Scientific Corp. The RPM system is currently used in the treatment of cardiac arrhythmia to define cardiac anatomy, map cardiac electrical activity, and guide an ablation catheter to a treatment site in a patient's heart.

In order to properly display the local image within the global image (however generated), both the local image and the global image are registered in a three-dimensional coordinate system. If the global image is a three-dimensional computer-generated representation of the body tissue, it is typically already registered within a three-dimensional coordinate system. Registration of the local image within the three-dimensional coordinate system can be accomplished by mounting a location sensor on the imaging catheter a known distance from the rotating ultrasound transducer, so that the three-dimensional coordinates of the ultrasound transducer, and thus, the origin of the local image can be determined. Depending on the type of location sensor, up to five degrees of freedom (x, y, z, pitch, and yaw) can be determined for the local image.

For example, a plurality of ultrasound sensors, such as those disclosed in U.S. patent application Ser. No. 09/128,304 to Willis et al. entitled "A dynamically alterable three-dimensional graphical model of a body region," can be mounted along the distal end of the imaging catheter. The geometry of the distal end of the imaging catheter can be extrapolated from the determined positional coordinates of the ultrasound transducers, so that the three positional coordinates (x, y, z) and two rotational coordinates (pitch and yaw) of the imaging element can be determined.

As another example, a magnetic sensor, such as those disclosed in U.S. Pat. No. 5,391,199 to Ben-Haim, entitled "Apparatus and Method for Treating Cardiac Arrhythmias," can be mounted at the distal end of the imaging catheter. Theoretically, these magnetic sensors can be used to determine six degrees of freedom, including roll. Because the roll of a rotating imaging element relative to the distal end of the imaging catheter is not known, however, the roll of the imaging element within the three-dimensional coordinate system cannot currently be determined using the magnetic sensors alone. It would be theoretically possible to mount the magnetic sensor on the rotating shaft to determine the roll of the rotating imaging element. Because these magnetic sensors are relatively large, however, such an arrangement is typically not practical.

As a result, it may be difficult to properly orient an image generated by a rotating imaging element. There thus remains a need for an improved system and method for properly orienting such an image.

SUMMARY OF THE INVENTION

In accordance with a first aspect of the present inventions, a method of determining the rotation of an operative element is provided. By way of non-limiting example, the operative element can be an imaging element, such as, e.g., an ultrasound transducer. Other types of associated operative elements, however, are contemplated by the present inventions.

The method comprises introducing the operative element within the body of a patient, rotating the operative element about an axis, and transmitting a tracking beam (such as, e.g., an ultrasound tracking beam) in mechanical association with the operative element. For example, the tracking beam can be transmitted from the rotating operative element or transmitted from an element mechanically coupled to the rotating operative element. The significance is that the tracking beam rotates with the operative element.

The method further comprises determining an angle through which the tracking beam rotates between a reference rotational orientation and a reference point. As an example, the reference point may be located within the patient. In the preferred method, the tracking beam is fan-shaped. For example, the tracking beam can exhibit a relatively small in-plane beamwidth (i.e., beamwidth within the plane of rotation) to provide the desired beam resolution, but exhibit a relative large out-of-plane beamwidth (i.e., beamwidth perpendicular to the plane of rotation) to increase the chance that the tracking beam will be received at the reference point.

Determination of the tracking beam rotation angle may be performed during operation or non-operation of the operative element. By way of non-limiting example, the angle determination can be accomplished by pulsing the tracking beam, and counting the number of tracking beam pulses transmitted as the tracking beam rotates from the reference rotational orientation to the reference point. In this case, the tracking beam can be considered to be rotated to the reference point when the highest magnitude tracking beam pulse intersects the reference point.

The method may further comprise associating the reference rotational orientation with a fiducial operating point of the operative element. For example, if the operative element is an imaging element, the fiducial operating point can be the transmission of a specific ultrasound imaging pulse that corresponds with a portion of the image. By way of non-limiting example, this association can allow the rotational orientation of the generated image to be corrected based on the tracking beam rotation angle.

In accordance with a second aspect of the present inventions, a medical system comprises an elongate member configured for introduction into the body of a patient, and a rotatable operative element mounted on the elongate member. As previously discussed, the operative element may be an imaging element, such as, e.g., an ultrasound transducer, and the elongate member can be a catheter member, although all types of rotatable operative elements and medical probes are contemplated by the present inventions.

The medical system further comprises a tracking element that is mechanically associated with the operative element and is configured for transmitting a tracking beam. The medical system further comprises a reference element that can be, e.g., located on another elongate member configured to be introduced into the body of the patient. In the preferred embodiment, the tracking beam is a fan-shaped beam, which may exhibit the previously described beamwidth characteristics.

The medical system further comprises processing circuitry configured for determining an angle through which the tracking beam rotates between a reference rotational orientation and the reference point. The processing circuitry can be configured to perform the angle determination during operation or non-operation of the operative element. As previously described, the tracking beam can be pulsed, in which case, the processing circuitry can be configured for counting the number of tracking beam pulses transmitted as the tracking beam rotates from the reference rotational orientation to the reference point. The processing circuitry may be further configured to associate the reference rotational orientation with a fiducial operating point of the operative element.

In accordance with a third aspect of the present inventions, a medical probe comprises an elongate member (such as, e.g., a catheter member) configured for introduction into the body of a patient, a rotatable operative element (such as, e.g., an imaging element) mounted on the elongate member, and a tracking element (such as, e.g., an ultrasound transducer) mechanically associated with the operative element and configured for generating a fan-shaped beam. This fan-shaped beam may exhibit the previously described beamwidth characteristics. The medical probe can optionally comprise a mismatched material partially covering the element to increase the out-of-plane beamwidth of the fan-shaped beam.

In accordance with a fourth aspect of the present inventions, an imaging medical probe comprises an elongate member configured for introduction into the body of a patient, a rotatable imaging element mounted on the elongate member (such as, e.g., a catheter body) and being configured for transmitting an imaging beam having a first out-of-plane beamwidth, and a diffraction grating slidably mounted on the elongate member and being configured to selectively mask the imaging element, so that the imaging element transmits a tracking beam having a second out-of-plane beamwidth greater than the first out-of-plane beamwidth. In the preferred embodiment, the imaging element comprises an ultrasound transducer, in which case, the diffraction grating can comprises a sonotranslucent window through which the ultrasound transducer can transmit an ultrasound tracking beam. In the preferred embodiment, the tracking beam is a fan-shaped beam, which may exhibit the previously described beamwidth characteristics.

In accordance with a fifth aspect of the present inventions, a method of orienting an image data acquired by an imaging assembly is provided. By way of non-limiting example, the imaging assembly can comprise an ultrasound transducer and the image data can be ultrasound image data. Other types of imaging assemblies, however, are contemplated by the present inventions.

The method comprises introducing the imaging assembly within the body of a patient, rotating the imaging assembly about an axis, and transmitting a tracking beam (such as, e.g., an ultrasound tracking beam) in mechanical association with the rotating imaging assembly. For the example, the tracking beam can be transmitted from the rotating imaging assembly or from an element mechanically coupled to the rotating imaging assembly. In the preferred method, the tracking beam is fan-shaped, which may exhibit the previously described beamwidth characteristics.

The method further comprises orienting the image data based on the rotation of the tracking beam. For example, the method may comprise determining an angle through which the tracking beam rotates between a reference rotational orientation and the reference point, in which case, the image data can be oriented an angle that is a function of the determined tracking beam rotation angle. This angle determination may be performed as previously described. The reference rotational orientation may be associated with a fiducial orientation within the image data, so that the image data can more easily be oriented.

In the preferred method, an imaging beam is transmitted from the rotating imaging assembly to generate the image data. In this case, the tracking and imaging beams may be the same beam or different beams. If different, the imaging beam can be rotationally offset from the tracking beam a predetermined angle, in which case, the orientation of the image data can be further based on the predetermined offset angle. In this case, the image data can be oriented an angle equal to a function of the difference between the determined tracking beam rotation angle and the predetermined offset angle.

The method can optionally comprise establishing a three-dimensional coordinate system, and displaying the image data in the three-dimensional coordinate system.

In accordance with a sixth aspect of the present inventions, an imaging medical system comprises an elongate member configured for introduction into the body of a patient, and a rotatable imaging assembly mounted on the elongate member and configured for acquiring image data. The imaging assembly may comprise an ultrasound transducer, and the elongate member can be a catheter member, although all types of rotatable imaging assemblies and medical probes are contemplated by the present inventions.

The medical system further comprises a tracking element that is mechanically associated with the imaging assembly and is configured for transmitting a tracking beam. In the preferred embodiment, the tracking beam is a fan-shaped beam, which may exhibit the previously described beamwidth characteristics. The imaging medical system further comprises processing circuitry configured for orienting the imaging data based on the rotation of the tracking beam. The imaging medical system may optionally comprise a display coupled to the processing circuitry for displaying the oriented image data.

The medical system may comprise a reference element for receiving the tracking beam. As previously described, the reference element can be, e.g., located on another elongate member configured to be introduced into the body of the patient. In this case, the processing circuitry can be configured for determining an angle through which the tracking beam rotates between a reference rotational orientation and the reference element. The processing circuitry can be configured to perform the angle determination during operation or non-operation of the operative element. As previously described, the tracking beam can be pulsed, in which case, the processing circuitry can be configured for counting the number of tracking beam pulses transmitted as the tracking beam rotates from the reference rotational orientation to the reference transducer. The processing circuitry may be further configured to associate the reference rotational orientation with a fiducial imaging pulse or rotational orientation within the image data.

In the preferred embodiment, the imaging assembly comprises an imaging element configured for transmitting an imaging beam. In this case, the imaging and tracking elements may be the same or different elements. If different elements, the imaging element can be rotationally offset from the tracking element a predetermined angle, in which case, the processing circuitry can be further configured to orient the image data based on the predetermined offset angle. For example, the processing circuitry can orient the image data an angle equal to a function of the difference between the determined tracking beam rotation angle and the predetermined offset angle.

The processing circuitry can optionally be configured for establishing a three-dimensional coordinate system, and displaying the image data within the three-dimensional coordinate system.

Other objects and features of the present invention will become apparent from consideration of the following description taken in conjunction with the accompanying drawings.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Figure 1:
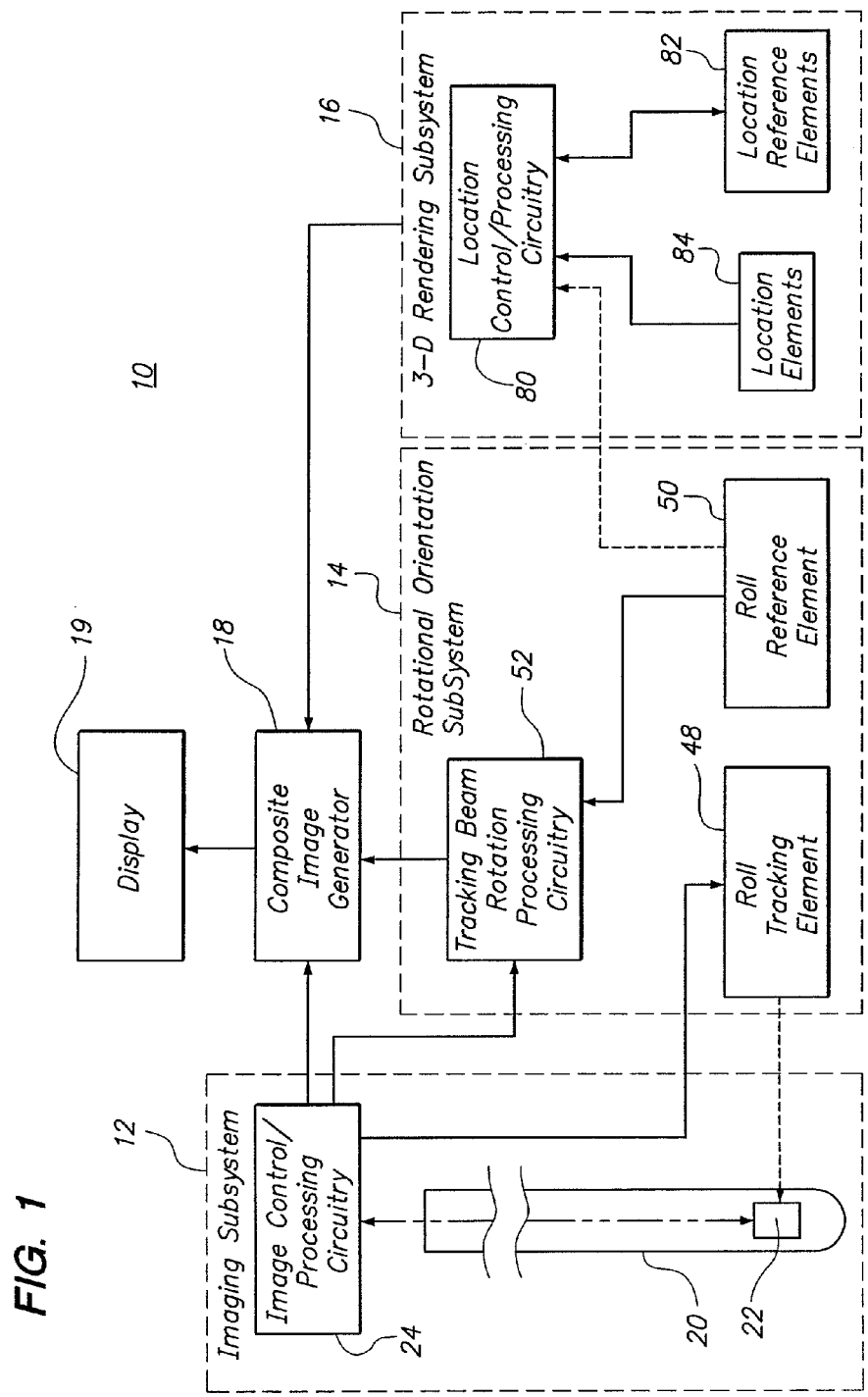
FIG. 1 is a functional block diagram of one preferred embodiment of a body tissue imaging system constructed in accordance with the present inventions.

Referring to FIG. 1, an exemplary body tissue imaging system 10 constructed in accordance with the present inventions is shown. The imaging system 10 generally comprises (1) an imaging subsystem 12 for generating image data of body tissue, e.g., a heart; (2) a rotational orientation subsystem 14 for determining the proper rotational orientation of the generated image data; (3) a three-dimensional rendering subsystem 16 for generating three-dimensional graphical data of the environment in which the imaged body tissue is contained; (4) a composite image generator 18 for properly orienting the generated image data based on the rotational orientation determined by the rotational orientation subsystem 14, and generating a composite image by superimposing the properly oriented image data within the three-dimensional graphical data generated by the three-dimensional rendering subsystem 16; and (5) a display 20 for displaying the composite image. It should be noted that the elements illustrated in FIG. 1 are functional in nature, and are not meant to limit the structure that performs these functions in any manner. For example, several of the functional blocks can be embodied in a single device, or one of the functional blocks can be embodied in multiple devices. Also, the functions can be performed in hardware, software, or firmware.

Figure 2:
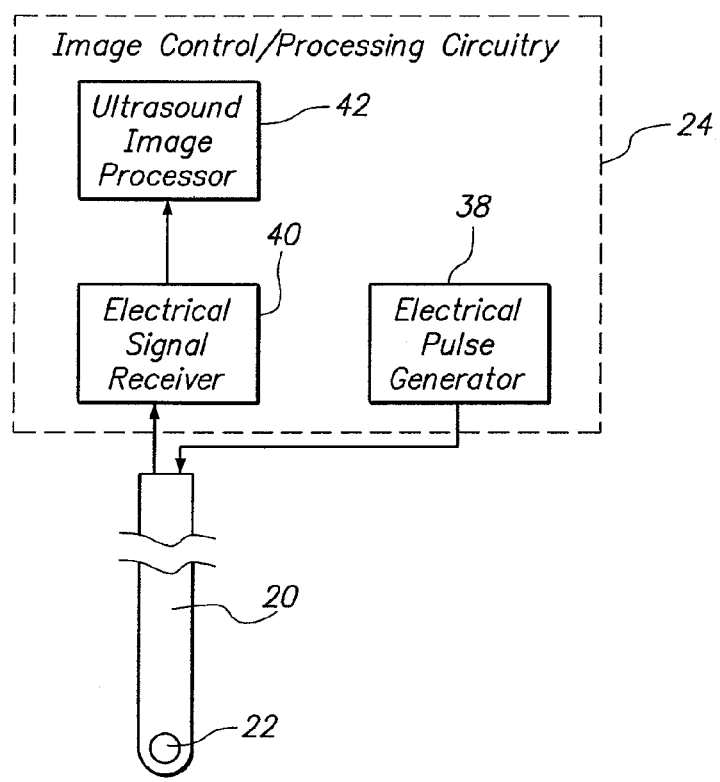
FIG. 2 is a functional block diagram of an ultrasound-based imaging subsystem used in the body tissue imaging system of FIG. 1.
Figure 3:
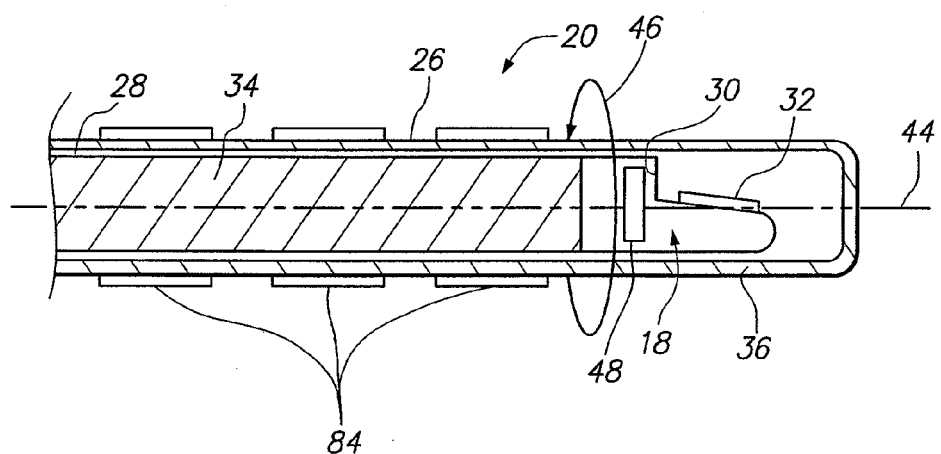
FIG. 3 is a cross-sectional view of an ultrasonic imaging catheter used in the ultrasound-based imaging subsystem of FIG. 2.

The imaging subsystem 12 generally comprises an imaging catheter 20, which includes a distally mounted rotatable imaging assembly 22 that generates and detects signals representing the interior of the body, and image control/processing circuitry 24 coupled to the imaging catheter 20 for processing these signals into image data. Referring now to FIGS. 2 and 3, the imaging subsystem 12 is described in further detail. In the illustrated embodiment, the imaging subsystem 12 is ultrasound-based, in which case, the imaging catheter 20 takes the form of an ultrasound imaging catheter, and the image control/processing circuitry takes the form of ultrasound imaging control/processing circuitry.

The ultrasound imaging catheter 20 comprises an elongated catheter body or sheath 24 having a lumen 28 extending therethrough. The catheter body 26 is made of a flexible material, so that it is able to be easily introduced through a body lumen, such as, e.g., an esophagus or a blood vessel. The rotatable imaging assembly 22 comprises a housing 30 (or "can") and an imaging element 32, and specifically an ultrasound imaging transducer, mounted therein. The imaging catheter 20 further comprises a drive shaft 34 extending through the lumen 28. The rotating imaging assembly 22 is mounted on the distal end of the drive shaft 34, and a drive motor (not shown) is mounted to the proximal end of the drive shaft 34. The catheter body 26 includes an acoustic window 36 for allowing ultrasound pulses to pass through the catheter body 26. The lumen 28 may be filled with fluid, e.g., water, to better couple ultrasound energy from the imaging element 32 to the surrounding body.

The image control/processing circuitry 24 includes an electrical pulse generator 38 and an electrical signal receiver 40, both of which are coupled to the imaging element 32 via signal wires (not shown) that extend through the center of the drive shaft 34. The image control/processing circuitry 24 further includes an ultrasound image processor 42 coupled to the electrical signal receiver 40.

To obtain an ultrasound image of the interior of the body, the imaging catheter 20 may be inserted into the body or placed on the skin surface of the body with the imaging element 32 adjacent the tissue to be imaged, and the imaging assembly 22 is operated to generate an imaging beam that rotates about an axis 44 and forms a rotational plane 46. Specifically, the imaging assembly 22 is mechanically rotated along the axis 44, while the pulse generator 38 transmits electrical pulses through the signal wires to excite the imaging element 32. In the illustrated embodiment, the imaging assembly 22 is rotated at 30 revolutions/second, and the pulse generator 38 generates 9 MHz pulses at a rate of 256 pulses per revolution. The imaging element 32 converts the electrical pulses into pulses of ultrasound energy, which are emitted into the body tissue. A portion of the ultrasound energy is reflected off of the body tissue back to the transducer 30. The imaging element 32 converts the back-reflected ultrasound energy into electrical signals representing the body tissue, which are transmitted back through the signal wires to the electrical signal receiver 40. The electrical signals are detected by the electrical signal receiver 40 and outputted to the ultrasound image processor 42, which processes the received electrical signals into 360 degree cross-sectional ultrasound image data of the body using known ultrasound image processing techniques. For each cross-section of image data, the ultrasound image processor 42 selects a fiducial orientation (in the illustrated embodiment, that associated with the generation of the first pulse) that will be used to orient the imaging data, as will be described in further detail below.

To image a three-dimensional volume of the body, the imaging assembly 22 may be translated axially within the catheter body 26 by pulling back the drive shaft 34 with the drive motor. Alternatively, the entire catheter body 26, with the imaging assembly 22, can be pulled back. As the imaging assembly 22 is axially translated, the imaging element 32 is rotated to obtain multiple cross-sectional images (i.e., "slices") of the body tissue at different positions within the body. In this case, the ultrasound image processor 42 then aggregates (i.e., pieces together) the multiple cross-sectional images to reconstruct the volume of the body using known volume reconstruction techniques.

Referring back to FIG. 1, the rotational orientation subsystem 14 comprises a roll tracking element 48 that is mechanically associated with the imaging assembly 22 and is configured for generating a tracking beam that rotates with the imaging assembly 22. Specifically, the roll tracking element 48 takes the form of an ultrasound transducer that is mounted within the housing 30 and is rotationally offset from the imaging element 32 at 90 degrees, as illustrated in FIG. 3. In this manner, the cross-coupling from the roll tracking element 48 to the imaging element 32 is minimized. Other rotational offsets, such as, e.g., 180 degrees, can be envisioned, but an offset of 90 degrees provides certain manufacturing advantages. In particular, the backing layer for each of the transducers can be designed without taking into account the effects of the other backing layer, which may otherwise be a concern if the transducers were offset from each other 180 degrees.

Figure 4:
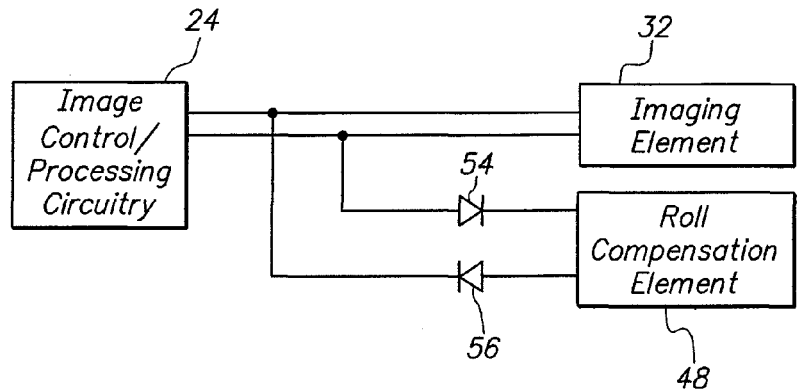
FIG. 4 is a schematic drawing of an electrical circuit used for minimizing interference produced by a tracking beam generated in the ultrasound imaging catheter of FIG. 3.

For purposes of manufacturing efficiency, the roll tracking element 48 and imaging element 32 are both wired to the image control/processing circuitry 24 in parallel, so that a single electrical pulse transmitted up the signal wires simultaneously excites both transducers, as illustrated in FIG. 4. To prevent return pulses from the tracking beam from interfering with the imaging data, the transducers can be operated at separate frequencies.

Alternatively or optionally, a diode 54 may be coupled to one of the wires leading to the roll tracking element 48, thereby allowing the high voltage transmit pulse to pass through to the roll tracking element 48, but preventing low-level received pulses from corrupting the receive signals from the imaging element 32. A second diode 56 may be coupled to the other wire leading to the roll tracking element 48 to balance the circuit and prevent unwanted noise. As another alternative, the image control/processing circuitry 24 can time multiplex the electrical pulses transmitted to the respective transducers if the resulting slowdown in the imaging transmit rate (and hence rotation speed of the imaging assembly 22) can be tolerated. Of course, the transducers can be wired to separate pulse generation circuits with the accompanying disadvantage of requiring additional hardware.

Referring still to FIG. 1, the image orientation circuitry 14 further comprises a roll reference element 50 that is configured for receiving the rotating tracking beam generated by the roll tracking element 48. To this end, the roll reference element 50 takes the form of an ultrasound transducer that is located within the path of the tracking beam. For example, the roll reference element 50 can be mounted to another catheter, as will be described in further detail later. To ensure that the roll reference element 50 is placed within the path of the tracking beam, the tracking beam is preferably fan-shaped.

Figure 5:
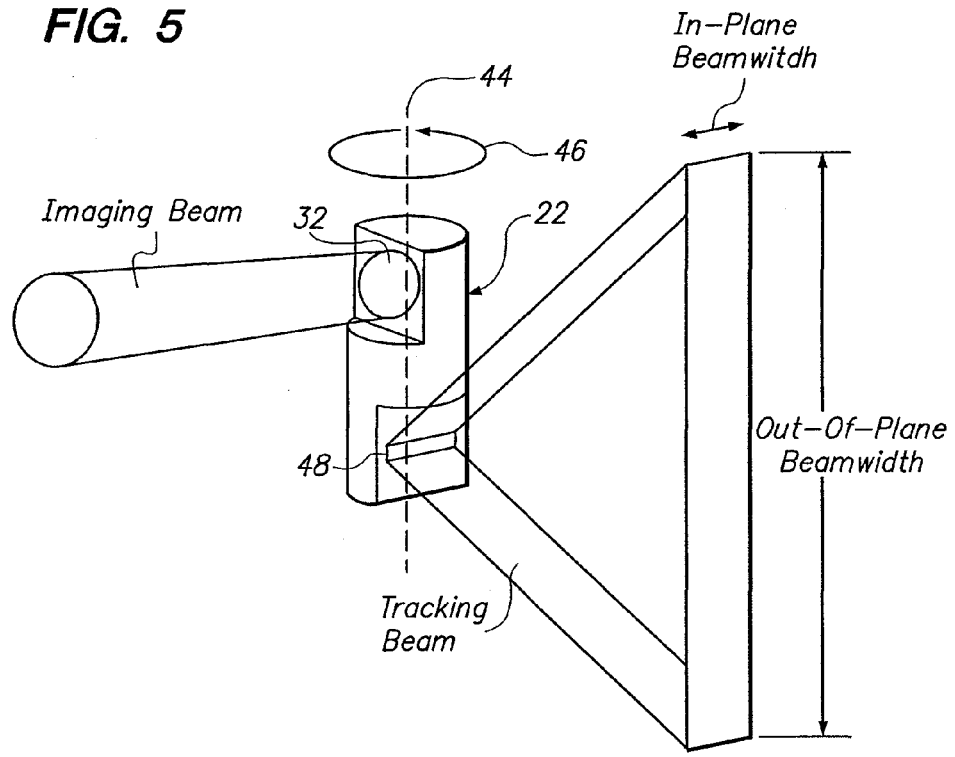
FIG. 5 is a perspective view of an imaging assembly used in the ultrasound imaging catheter of FIG. 3, wherein the beamwidth characteristics of the imaging and tracking beams are particularly shown.

Specifically, as illustrated in FIG. 5, the axial dimension of the roll tracking element 48 is relatively small (e.g., less than one wavelength), so that the tracking beam exhibits a relatively large out-of-plane beamwidth (i.e., width of the beam perpendicular to the rotational plane 46). In this manner, the roll reference element 50 has an increased chance of receiving the tracking beam regardless of its location. Preferably, the out-of-plane beamwidth of the tracking beam is greater than 90 degrees, and most preferably, substantially equal to 180 degrees, so receipt of the tracking beam is ensured. As an additional advantage, the increased out-of-band beamwidth provides a divergent beam that minimizes significant image degradation. The narrow axial dimension of the roll tracking element 48 can be conveniently achieved by masking a larger transducer with a mismatched material, such as, e.g., an air-filled material.

In contrast, the transverse dimension of the roll tracking element 48 is relatively large, so that the tracking beam exhibits a relatively small in-plane beamwidth (i.e., the width of the beam parallel to the rotational plane 46). In this manner, the resolution of the tracking beam is increased. Preferably, the in-plane beamwidth of the tracking beam is less than 10 degrees, and most preferably, less than 5 degrees. However, the width and thickness of the roll tracking element 48 should be about the same as that of the imaging element 32, to ensure that the resolutions of the tracking and imaging beams are equivalent. Thus, it can be appreciated that the roll tracking element 48 generates a fan-shaped beam that exhibits a narrow in-plane beamwidth and a broad out-of-plane beamwidth.

Although the imaging orientation subsystem 14 has been described as using a separate roll tracking element for generating a tracking beam, it is possible to use the imaging element 32 to generate the tracking beam. In this case, care would have to be taken to locate the roll reference element 50 within the path of the relatively narrow imaging/tracking beam. Alternatively, a diffraction grating can be placed over the imaging element 32, so that a fan-shaped tracking beam can be generated.

Figure 6:
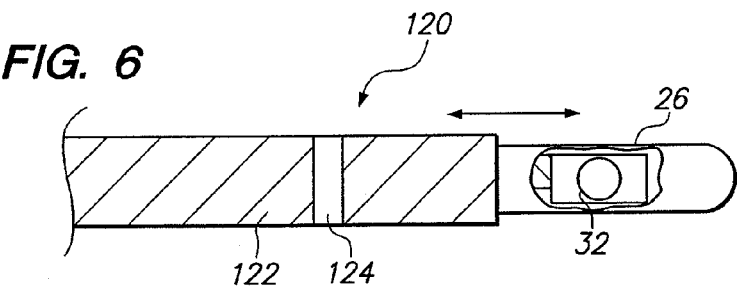
FIG. 6 is a partially cut-away plan view of another ultrasound image catheter used in the ultrasound-based imaging subsystem of FIG. 2, wherein a slidable diffraction grating can be used selectively generate an imaging beam and tracking beam.
Figure 7:
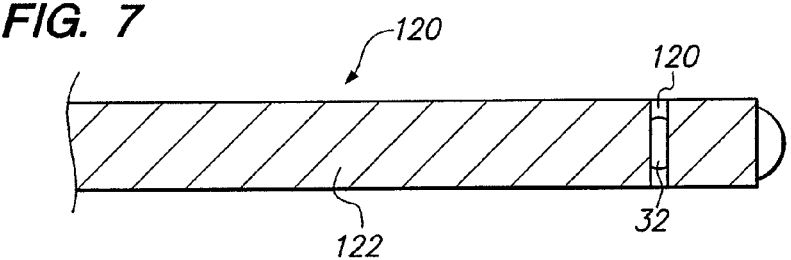
FIG. 7 is a partially cut-away plan view of the ultrasound imaging catheter of FIG. 6, wherein the diffraction grating is shown covering the imaging element, so that a fan-shaped tracking beam is generated.

For example, FIG. 6 illustrates an alternative embodiment of an imaging catheter 120 that employs a diffraction grating 122 that is generally composed of an ultrasonically mismatched material, e.g., an air impregnated material, and comprises a sonotranslucent window 124 through which ultrasound energy can be transmitted. The diffraction grating 122 is slidably mounted on the catheter body 26, such that it can be selectively translated distally over the imaging element 32 during an image orientation procedure (FIG. 6), and translated proximally to uncover the imaging element 32 during an imaging procedure (FIG. 5). The sonotranslucent window 124 has a relatively small axial dimension and a relatively large transverse dimension, so that a fan-shaped tracking beam is generated.

Figure 8:
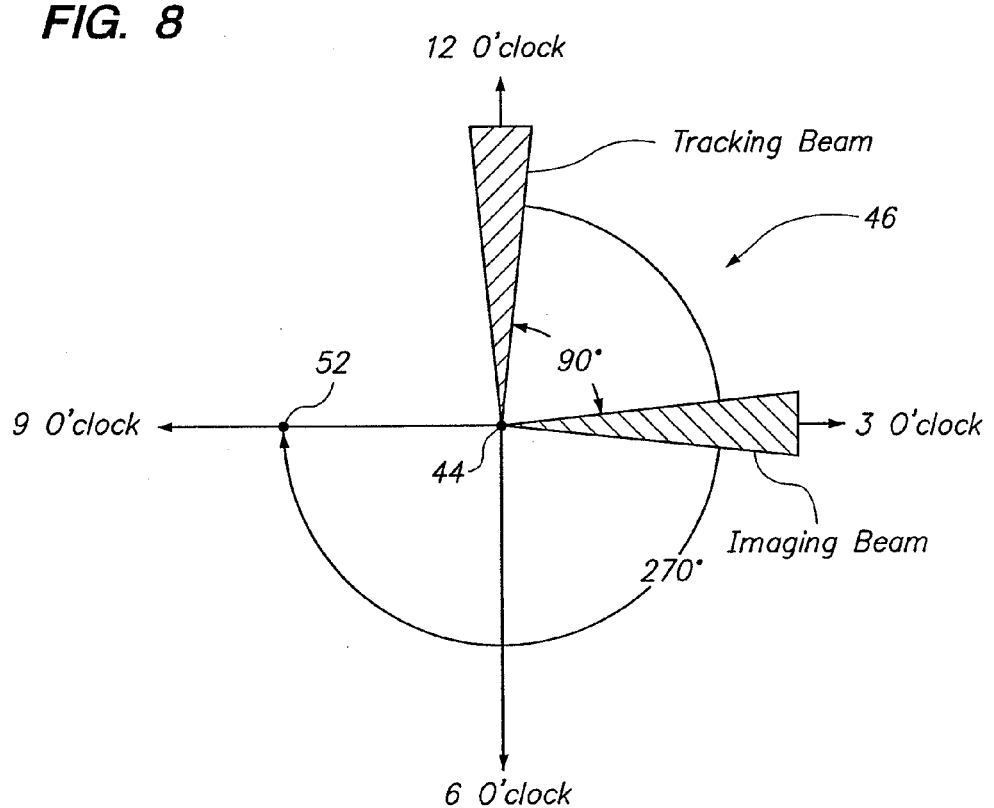
FIG. 8 is a diagram of the rotational coordinate system established by the rotational plane processing circuitry used in the body tissue imaging system of FIG. 1, wherein exemplary rotational orientations of the imaging beam, tracking beam, and roll reference element are particularly shown.

Referring back to FIG. 1, the rotational orientation subsystem 14 further comprises tracking beam rotation processing circuitry 52 configured for determining the angle through which the tracking beam rotates between a reference angular orientation and the roll reference element 50. The reference angular orientation is the angular orientation of the tracking beam associated with the fiducial orientation of the ultrasound image, which in this case, is the image sector associated with the first electrical pulse in each revolution. The tracking beam rotation processing circuitry 52 is coupled to the image control/processing circuitry 24 to obtain this information. For example, FIG. 8 further illustrates an exemplary angular orientation between the tracking beam and roll reference element 50 within the rotational plane 46. In this example, the rotational orientation of the roll reference element 50 is shown in a 9 o'clock position, and the rotational orientations of the tracking and imaging beams associated with the fiducial orientation of the image data (i.e., the orientations when the first electrical pulse of the current revolution has been generated) are shown in 12 and 3 o'clock positions, respectively. As can seen, the angle through which the tracking beam rotates between the reference angular orientation (here, 12 o'clock position) and the roll reference element 50 (here, 9 o'clock position) is 270 degrees.

The tracking beam rotation processing circuitry 52 calculates this angle by counting a number of tracking beam pulses transmitted during a time period defined by the rotation of the tracking beam from the reference angular orientation to the roll reference element 50. That is, the first tracking beam pulse will be that corresponding to the 12 o'clock position of the ultrasound image, and the last tracking beam pulse will be that received by the roll reference element 50. This process will be described in further detail below.

Figure 9:
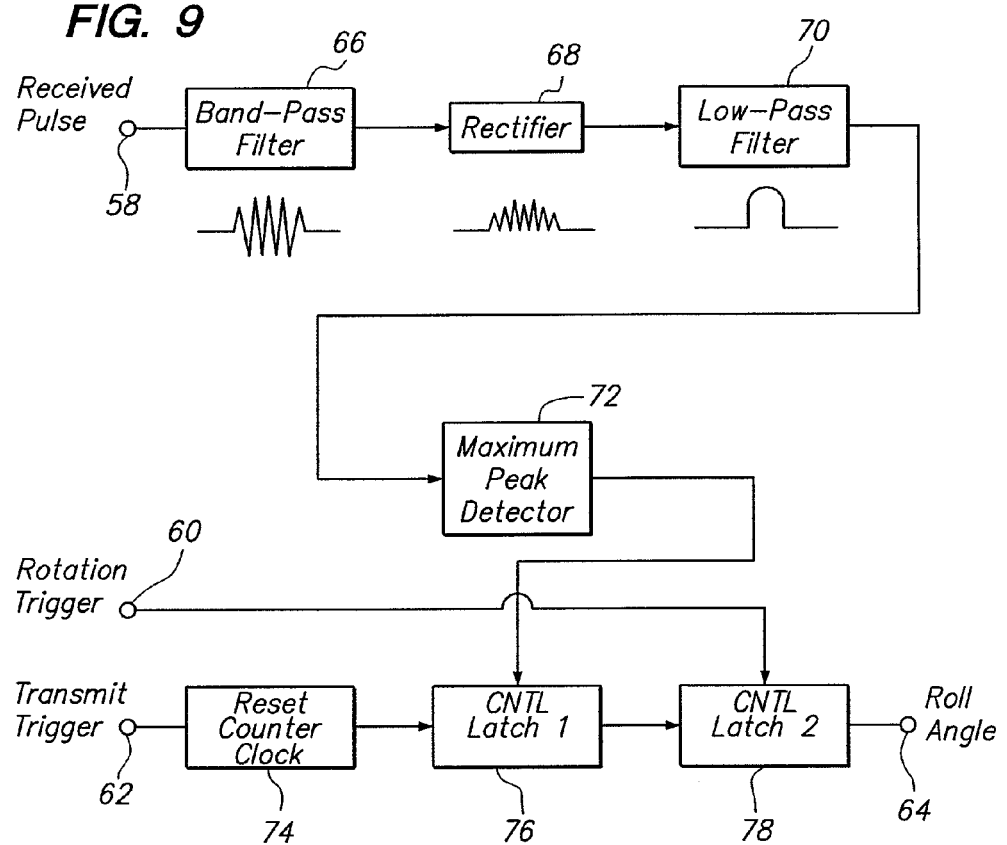
FIG. 9 is a block diagram of the tracking beam rotation processing circuitry used in the body tissue imaging system of FIG. 1.

Referring to FIG. 9, the tracking beam rotation processing circuitry 52 is illustrated in further detail. The circuitry 52 comprises (1) a tracking beam input 58 for acquiring signals received by the roll reference element 50 (and specifically tracking beam pulses); (2) a rotation trigger input 60 for acquiring a reference trigger signal from the image control/processing circuitry 24 indicating each time the ultrasound imaging pulse (in this case, the first pulse) associated with the fiducial orientation of the image data is generated (one time per rotation); (3) a transmit trigger input 62 for acquiring a pulse transmission trigger signal from the image control/processing circuitry 24 indicating each time an ultrasound imaging pulse is generated (256 times per rotation); and (4) an output 64 for outputting the tracking beam rotation angle in the form of a digital count between 1 and 256.

At the tracking beam input 58, the tracking beam rotation processing circuitry 52 comprises a bandpass filter 66 (and specifically a 9 MHz bandpass filter) for outputting a substantially noise-free tracking beam pulse. The processing circuitry 52 further comprises a rectifier 68 for outputting the absolute value of the tracking beam pulse components, so that the negative portion of the tracking pulse, which may contain the majority of the energy, can be later detected. The processing circuitry 52 further comprises a low pass filter 70 for outputting a low frequency signal correlated to the magnitude of the tracking beam pulse, and a maximum peak detector 72 for sensing the peak of this low frequency signal. Notably, the low pass filter 70 simplifies and makes the maximum peak detector 72 more accurate, which may otherwise be difficult to accomplish with high frequency signals.

The maximum peak detector 72, until reset, will store the maximum peak of the lower frequency signals received from the low pass filter 70, i.e., it will only store the peak amplitude of a lower frequency signal correlated to the current tracking pulse if it is greater than the previously stored peak amplitude. The maximum peak detector 72 will output a signal (e.g., high) if the peak amplitude of the current pulse is greater than the currently stored maximum peak amplitude. Thus, for each revolution, the maximum peak detector 72 will continue to output a high up until the tracking beam intersects the roll reference element 50, and will output a low thereafter. In essence, the maximum peak detector 72 indicates when the tracking beam intersects the roll reference element 50, e.g., at the transition from a high output to a low output. The rotation trigger input 60 is coupled to the reset of the maximum peak detector 72, so that it is reset to "0" once the imaging assembly 22 makes a full revolution.

At the transmit trigger input 62, the tracking beam rotation processing circuitry 52 comprises a counter 74. Thus, the counter 74 will increment by "1" each time a tracking beam pulse is generated. The rotation trigger input 60 is coupled to the reset of the counter 74, so that the counter is reset to "0" once the imaging assembly 22 makes a full revolution. The tracking beam rotation processing circuitry 52 further comprises a first latch 76 for latching in the current count from the counter 74. The output of the maximum peak detector 72 is coupled to the control input of the first latch 76, so that it outputs the current count each time the amplitude of the current tracking beam pulse is greater than the currently stored maximum amplitude (the maximum peak detector 72 outputs a logical high), i.e., the tracking beam has not yet intersected the roll reference element 50, and stops outputting the current count each time the amplitude of the current tracking beam pulse is less than the maximum stored amplitude (the maximum peak detector 72 outputs a logical low), i.e., the tracking beam has already intersected the roll reference element 50. The tracking beam rotation processing circuitry 52 further comprises a second latch 78 coupled to the output of the first latch 76 for latching in the count outputted from the first latch 76. The rotation trigger input 60 is coupled to the control input of the second latch 78, so that the second latch 78 outputs the final count once the imaging assembly 22 makes a full revolution. This count represents the angle through which the tracking beam rotated. For example, if the count is 64, the angle of rotation will be 90 degrees. If the count is 128, the angle of rotation will be 180 degrees, and so.

Figure 10:
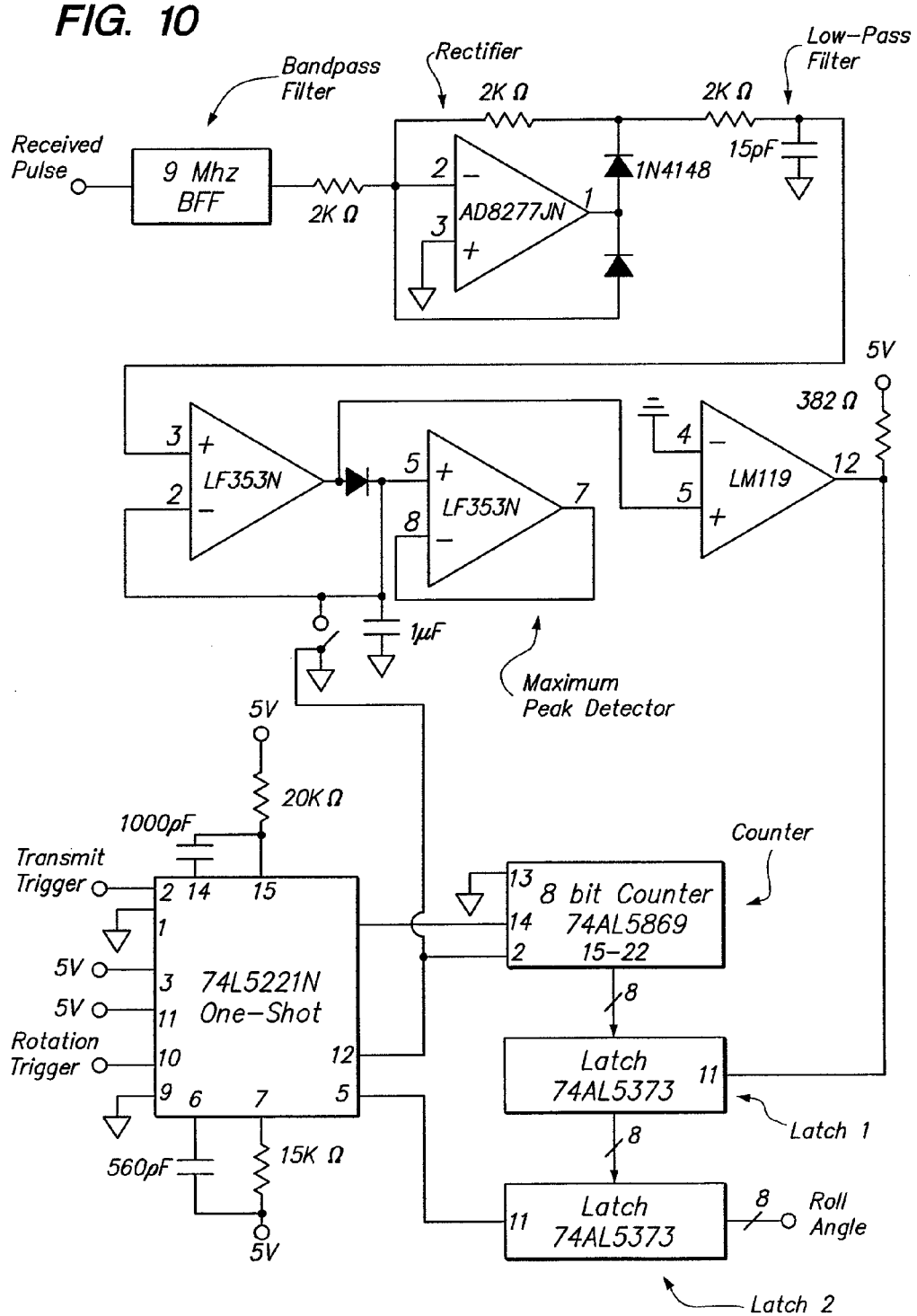
FIG. 10 is an electrical schematic particularly showing the detailed componentry of the tracking beam rotation processing circuitry illustrated in FIG. 9.

The detailed implementation of the FIG. 9 block diagram is illustrated in FIG. 10. Component model numbers and values are only meant to exemplify one specific implementation of the tracking beam rotation processing circuitry 52, and are not meant to limit the present invention in any manner.

Referring back to FIG. 1, the three-dimensional rendering subsystem 16 comprises location control/processing circuitry 80 configured for establishing a three-dimensional coordinate system by controlling and processing signals transmitted between spaced apart location reference elements 82 coupled to the circuitry 80. In essence, the three-dimensional coordinate system provides an absolute framework in which all spatial measurements will be taken. The circuitry 80 is further configured for using location elements 84 to determine the positional coordinates of points of interest within the three-dimensional coordinate system. Specifically, the circuitry 80 is configured for determining the positional coordinates (x,y,z) of the roll reference element 50 within the three-dimensional coordinate system. Depending on the specific implementation, the circuitry 80 can determine this information from the roll reference element 50 itself or from a location element 84 positioned adjacent the roll reference element 50. The circuitry 80 is further configured for determining the positional coordinates (x,y,z) and orientation (pitch, yaw) of the rotational axis 44 within the three-dimensional coordinate system, as well as the positional coordinates (x,y,z) of the imaging element 32, and thus the origin of the rotational plane 46, within the three-dimensional coordinate system. Depending on the specific implementation, the circuitry 80 can determine this information based on the determined positional coordinates and orientation of a single location element 84 mounted on the distal end of the catheter body 26 or based on the determined positional coordinates of multiple location elements 84 mounted along the distal end of the catheter body 26.

In the illustrated embodiment, the location control/processing circuitry 80 is ultrasound-based, in which case, the location elements 84 and location reference elements 82 will take the form of ultrasound transducers. The roll reference element 50 or a location element adjacent the roll reference element 50 will also take the form of an ultrasound transducer. By virtue of its capability of receiving the ultrasound tracking beam from the roll tracking element 48, however, the roll reference element 50 already takes the form of an ultrasound transducer, and thus, it can conveniently be used as a location element. In this case, the dual ultrasound functionality of the roll reference element 50 can be time multiplexed if the decrease in processing speed can be tolerated. Otherwise, a separate location element 84 can be located adjacent the single-function reference element 50.

The location reference elements 82 can be mounted on a pair of reference catheters (not shown). For example, four reference elements 82 can be mounted on each reference catheter. The reference catheters can be placed anywhere within the body (preferably, a known location) that allows the reference elements 82 to communicate with the location elements 84 and roll reference element 50. For example, if the body tissue to be imaged is heart tissue, the reference catheters can be respectively located within the coronus sinus and the apex of the right ventricle of the heart. In the illustrated embodiment, three location elements 84 are mounted at the distal end of the imaging catheter body 26 (shown in FIG. 3), and the roll reference element 50 can be located on one of the reference catheters. Alternatively, the roll reference element 50 can be located on another catheter, e.g., a mapping catheter.

To establish the three-dimensional coordinate system and to determine the positions of the elements within that coordinate system, the location control/processing circuitry 80 operates to cause each location reference element 82 to transmit ultrasound pulses to the remaining reference elements 82, the location elements 84, and the roll reference element 50 in order to determine the distances between each transmitting reference element 82 and the other elements. The orientation control/processing circuitry 54 calculates the relative distances between the transducers using the "time of flight" and velocity of the ultrasound pulses therebetween. To simplify the distance computations, the velocity of the ultrasound pulses may be assumed to be constant. This assumption typically only produces a small error since the velocity of ultrasound pulses varies little in body tissue and blood. The three-dimensional coordinate system is established by triangulating the relative distance calculations between each reference element 82 and the remaining reference elements 82.

The coordinates of the location elements 84 and roll reference element 50 within this three-dimensional coordinate system are determined by triangulating the relative distance calculations between each of the location elements 84 and roll reference element 50, on the one hand, and the reference elements 82, on the other hand. Preferably, the orientation control/processing circuitry 54 determines the positions of the location elements 84 continually and in real time, which becomes significant when the rotating imaging assembly 22 is longitudinally translated. In the illustrated embodiment, the circuitry 54 determines these positions 15 times/second.

To prevent or minimize ultrasound interference that may otherwise result from the transmission of ultrasound energy from the ultrasound imaging assembly 22, the location control/processing circuitry 80 preferably includes filtering circuitry. For example, the emission of ultrasound energy from the imaging element 32 may cause the measured distance between a location reference element 82 and a location element 84 or roll reference element 50 to be less than it actually is. To minimize this adverse effect, multiple distance measurements between each combination of elements can be taken for each measurement cycle. The greatest distance measurement can then be selected from the multiple distance measurements to obtain the true measurement between the transducers. Such a filtering technique is disclosed in U.S. patent application Ser. No. 10/213,441, entitled "Performing Ultrasound Ranging in the Presence of Ultrasound Interference," which is fully and expressly incorporated herein by reference.

Once the positional coordinates of the location elements 84 have been determined, the location control/processing circuitry 80 can determine the positional coordinates and orientation of the rotational axis 44 and the positional coordinates of the origin of the rotational plane 46. Specifically, the location control/processing circuitry 80 can determine this information by extrapolating the determined positions of the location elements 84 based on the known structure of the imaging catheter body 26 and the positional relationship between the location elements 84 and imaging element 32.

Alternatively, the position of the imaging element 32, and thus the position of the origin of the rotational plane 46, can be determined by using the imaging element 32, itself, as an ultrasound location element. Specifically, the imaging element 32 can be operated in two different resonant modes that are associated with different frequencies, e.g., 9 MHz and 1 MHz. That is, the imaging element 32 can be operated in one resonant mode at 9 MHz to generate ultrasound imaging pulses, and can be operated in a second resonant mode at 1 MHz to generate ultrasound positioning pulses. The imaging element 32 can be conveniently operated in these two resonant modes by stimulating it with a single electrical pulse that exhibits harmonic frequencies corresponding to the resonant modes. The relatively short pulsewidth of the electrical pulses used to stimulate the imaging element 32 during the imaging function naturally contain harmonic frequencies that can stimulate both resonant modes of the imaging element 32. This technique is advantageous in that it compensates for any axial shifting ("creep") of the imaging element 32 relative to the catheter body. That is, because the imaging element 32 is being used to track itself, the positional coordinates of the imaging element 32, however axially shifted, can be accurately determined. Further details on this technique are disclosed in copending U.S. Pat. No. 6,719,700, entitled "Ultrasound Ranging For Localization of Imaging Element," which is fully and expressly incorporated herein by reference.

The location control/processing circuitry 84 is optionally configured to reconstruct the body cavity in which the image is generated by determining the positional coordinates of roving location elements that are placed in contact with the inner surface of the body cavity. Additional details on determining the location and orientation of ultrasound transducers and the catheters that carry them, as well as body cavity reconstruction techniques, can be found in U.S. patent application Ser. No. 09/128,304 to Willis et al. entitled "A dynamically alterable three-dimensional graphical model of a body region," which is fully and expressly incorporated herein by reference.

It should be noted that there are other means for determining the position and orientation of elements and catheters. For example, magnetic tracking technique, such as that disclosed in U.S. Pat. No. 5,391,199 to Ben-Haim, entitled "Apparatus and Method for Treating Cardiac Arrhythmias," which is fully and expressly incorporated herein by reference. In this magnetic technique, a single location element can be used to determine the positional coordinates (x,y,z) and orientation (pitch, yaw) of the structure on which it is mounted. As another example, a voltage tracking technique, such as that disclosed in U.S. Pat. No. 5,983,126, entitled "Catheter Location System and Method," both of which are fully and expressly incorporated herein by reference.

The composite image generator 18 is configured for superimposing the image data obtained from the image/control processing circuitry 24 over the three-dimensional information (including the positional coordinates of the roll reference element 50, positional coordinates and orientation of the rotational axis 44, and optional cavity reconstruction) from the three-dimensional rendering subsystem 16, and displaying the composite image data on the display 20. Significantly, the composite image generator 18 properly orients the image data about the rotational axis 44.

In particular, using standard mathematical transformation techniques, the composite image generator 18 transforms the positional coordinates of roll reference element 50 onto the rotational plane 46, as defined by the positional coordinates of the axis 44, and rotates the fiducial orientation of the image data from the roll reference element 50 (i.e., the absolute rotational orientation) an angle equal to the difference between the predetermined angular offset between the imaging and tracking beams and the tracking beam rotation angle. For example, referring back to the example in FIG. 8, the imaging beam is rotationally offset from the tracking beam 90 degrees (by virtue of the 90 degree mechanical offset between the imaging element 32 and roll tracking element 48) and the tracking beam rotation angle of 270 degrees. Thus, to determine the angle that the image data will be rotated, the composite image generator 18 will subtract the tracking beam rotation angle (270 degrees) from the angular offset between the imaging and tracking beams (90 degrees). Thus, in this example, the image data will be rotated by 90−270=−180 degrees.

It should be noted that the image need not be oriented and superimposed in context of the three-dimensional coordinate system, and the present inventions should not be so limited. For example, the roll reference element 50 can be deliberately located in a position that the physician deems to be the absolute rotational orientation (e.g. towards the ceiling, towards an anatomical landmark, etc.). Then, the image data can be rotated from this absolute rotational orientation an angle equal to the difference between the angular offset between the imaging and tracking beams and the tracking beam rotation angle, or alternatively, the physician can visually rotate the displayed image from the absolute rotational orientation by this angle.

In the foregoing specification, the invention has been described with reference to a specific embodiment thereof. It will, however, be evident that various modifications and changes may be made thereto without departing from the broader spirit and scope of the invention. For example, the reader is to understand that the specific ordering and combination of process actions shown in the process flow diagrams described herein is merely illustrative, and the invention can be performed using different or additional process actions, or a different combination or ordering of process actions. As another example, features known to those of skill in the art can be added to the embodiment. Other processing steps known to those of ordinary skill in the art may similarly be incorporated as desired. Additionally and obviously, features may be added or subtracted as desired. Accordingly, the invention is not to be restricted except in light of the attached claims and their equivalents.

What is claimed is:

1. A method of determining the rotation of an operative element, comprising:
    introducing the operative element into the body of a patient;
    rotating the operative element about an axis;
    transmitting a tracking beam in mechanical association with the rotating operative element;
    receiving the tracking beam at the reference point; and
    determining an angle through which the tracking beam rotates between a reference rotational orientation and a reference point based on the receipt of the tracking beam.

2. The method of claim 1, wherein the tracking beam is transmitted from the rotating operative element.

3. The method of claim 1, wherein the tracking beam is transmitted from an element mechanically coupled to the rotating operative element.

4. The method of claim 1, wherein the tracking beam is an ultrasound tracking beam.

5. The method of claim 1, wherein the reference point is located within the patient.

6. The method of claim 1, further comprising operating the operative element, wherein the angle determination is performed during operation of the operative element.

7. The method of claim 1, further comprising operating the operative element, wherein the angle determination is only performed during non-operation of the operative element.

8. The method of claim 1, wherein the tracking beam is fan-shaped.

9. The method of claim 1, wherein the tracking beam exhibits an out-of-plane beamwidth greater than ninety degrees.

10. The method of claim 1, wherein the tracking beam exhibits an out-of-plane beamwidth substantially equal to one hundred eighty degrees.

11. The method of claim 1, wherein the operative element comprises an imaging element.

12. The method of claim 11, wherein the imaging element comprises an ultrasound transducer.

13. The method of claim 1, wherein the reference point is fixed relative to the body of the patient.

14. A method of determining the rotation of an operative element carried by an elongate member having a longitudinal axis, comprising:
 introducing the operative element into the body of a patient;
 rotating the operative element relative to the elongate member about the longitudinal axis;
 transmitting a tracking beam in mechanical association with the rotating operative element; and
 determining an angle through which the tracking beam rotates between a reference rotational orientation and a reference point
 and the operative element is rotated relative to the elongate member about the longitudinal axis.

15. A method of determining the rotation of an operative element, comprising:
 introducing the operative element into the body of a patient;
 rotating the operative element about an axis;
 transmitting a tracking beam in mechanical association with the rotating operative element, wherein the tracking beam exhibits an in-plane beamwidth of less than ten degrees; and
 determining an angle through which the tracking beam rotates between a reference rotational orientation and a reference point.

16. The method of claim 15, wherein the tracking beam exhibits an in-plane beamwidth of less than five degrees.

17. A method of determining the rotation of an operative element, comprising:
 introducing the operative element into the body of a patient;
 rotating the operative element about an axis;
 transmitting a tracking beam in mechanical association with the rotating operative element; and
 determining an angle through which the tracking beam rotates between a reference rotational orientation and a reference point by counting the number of tracking beam pulses transmitted as the tracking beam rotates from the reference rotational orientation to the reference point.

18. The method of claim 17, wherein the tracking beam is considered to be rotated to the reference point when a highest magnitude tracking beam pulse intersects the reference point.

19. A method of determining the rotation of an operative element, comprising:
 introducing the operative element into the body of a patient;
 rotating the operative element about an axis;
 transmitting a tracking beam in mechanical association with the rotating operative element;
 determining an angle through which the tracking beam rotates between a reference rotational orientation and a reference point; and
 associating the reference rotational orientation with a fiducial operating point of the operative element.

20. A medical system, comprising:
 an elongate member configured for introduction into the body of a patient;
 a rotatable operative element mounted on the elongate member;
 a tracking element mechanically associated with the operative element, the tracking element configured for transmitting a tracking beam;
 a reference element; and
 processing circuitry configured for determining an angle through which the tracking beam rotates between a reference rotational orientation and the reference element.

21. The medical system of claim 20, wherein the tracking element is an ultrasound transducer.

22. The medical system of claim 20, further comprising another elongate member configured for introduction into the body of the patient, wherein the reference element is mounted on the other elongate member.

23. The medical system of claim 20, wherein the processing circuitry is further configured for determining the tracking beam rotation angle during operation of the operative element.

24. The medical system of claim 20, wherein the processing circuitry is further configured for determining the tracking beam rotation angle during non-operation of the operative element.

25. The medical system of claim 20, wherein the tracking element is configured for transmitting a fan-shaped tracking beam.

26. The medical system of claim 20, wherein the tracking element is configured for transmitting a tracking beam that exhibits an in-plane beamwidth of less than ten degrees.

27. The medical system of claim 20, wherein the tracking element is configured for transmitting a tracking beam that exhibits an in-plane beamwidth of less than five degrees.

28. The medical system of claim 20, wherein the tracking element is configured for transmitting a tracking beam that exhibits an out-of-plane beamwidth greater than ninety degrees.

29. The medical system of claim 20, wherein the tracking element is configured for transmitting a tracking beam that exhibits an out-of-plane beamwidth substantially equal to one hundred eighty degrees.

30. The medical system of claim 20, wherein the elongate member is a catheter member.

31. The medical system of claim 20, wherein the operative element is mounted on a distal end of the medical probe.

32. The medical system of claim 20, wherein the operative element comprises an imaging element.

33. The medical system of claim 32, wherein the imaging element comprises an ultrasound transducer.

34. The medical system of claim 20, wherein the processing circuitry is further configured for operating the tracking element to generate a pulsed tracking beam, for counting the number of tracking beam pulses transmitted as the tracking beam rotates from the reference rotational orientation to the reference element, and for determining the tracking beam rotation angle based on the counted number of tracking beam pulses.

35. The medical system of claim 34, wherein the processing circuitry is further configured for determining when a highest magnitude tracking beam pulse is received, wherein the tracking beam is considered to be rotated to the reference element when the highest magnitude tracking beam pulse intersects the reference element.

36. The medical system of claim 20, wherein the processing circuitry is further configured for associating the reference rotational orientation with a fiducial operating point of the operative element.

37. The medical system of claim 20, wherein the elongate member has a longitudinal axis, and operative element is configured for being rotated relative to the elongate member about the longitudinal axis.

38. The medical system of claim 20, wherein the reference element is configured for receiving the tracking beam, and the processing circuitry is configured for performing the tracking beam rotation determination is based on the receipt of the tracking beam.

39. The medical system of claim 20, wherein the reference element is configured for being fixed relative to the body of the patient.

* * * * *